US006699488B2

(12) United States Patent
Deckner et al.

(10) Patent No.: US 6,699,488 B2
(45) Date of Patent: Mar. 2, 2004

(54) RINSABLE SKIN CONDITIONING COMPOSITIONS

(75) Inventors: George Endel Deckner, Cincinnati, OH (US); Scott Edward Manchuso, Cincinnati, OH (US); William Joseph Monsueir, West Chester, OH (US); Victor Ruben Rodriguez, West Chester, OH (US); Mark Richard Sine, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/298,891

(22) Filed: Nov. 18, 2002

(65) Prior Publication Data

US 2003/0211061 A1 Nov. 13, 2003

Related U.S. Application Data

(63) Continuation of application No. 10/142,217, filed on May 9, 2002, now abandoned.

(51) Int. Cl.[7] .............................. A61K 7/00; A61K 7/42; A61K 31/74
(52) U.S. Cl. ...................... 424/401; 424/59; 424/78.02; 424/78.08; 424/400; 514/937; 514/938
(58) Field of Search ................................ 424/400, 401, 424/59, 78.02, 78.08; 514/937, 938

(56) References Cited

U.S. PATENT DOCUMENTS

| | | |
|---|---|---|
| 3,892,881 A | 7/1975 | Lissant |
| 4,389,418 A | 6/1983 | Burton |
| 4,606,913 A | 8/1986 | Aronson et al. |
| 5,004,598 A | 4/1991 | Lochhead et al. |
| 5,035,890 A | 7/1991 | Braun |
| 5,387,417 A | 2/1995 | Rentsch et al. |
| 5,534,265 A | 7/1996 | Fowler et al. |
| 5,618,522 A | 4/1997 | Kaleta et al. |
| 5,667,800 A | 9/1997 | De Vringer |
| 5,686,087 A | 11/1997 | Ansmann et al. |
| 5,747,011 A | 5/1998 | Ross et al. |
| 5,849,281 A | 12/1998 | Babinski et al. |
| 5,888,492 A | 3/1999 | Starch |
| 5,928,632 A | 7/1999 | Reusch |
| 6,150,403 A | 11/2000 | Biedermann et al. |
| 6,174,533 B1 | 1/2001 | SaNogueira, Jr. et al. |
| 6,183,766 B1 | 2/2001 | Sine et al. |
| 6,261,541 B1 | 7/2001 | Karpov et al. |
| 6,290,936 B1 | 9/2001 | Ross et al. |
| 6,342,208 B1 | 1/2002 | Hyldgaard et al. |
| 6,355,230 B2 | 3/2002 | Gers-Barlag et al. |
| 6,361,781 B2 | 3/2002 | Lorant |
| 6,410,035 B1 | 6/2002 | Gers-Barlag et al. |
| 2001/0022966 A1 | 9/2001 | Gers-Barlag et al. |
| 2001/0047039 A1 | 11/2001 | McManus et al. |
| 2002/0018789 A1 | 2/2002 | Bers-Barlag et al. |
| 2002/0022007 A1 | 2/2002 | Gers-Barlag et al. |
| 2003/0049282 A1 | 3/2003 | Aronson et al. |
| 2003/0054019 A1 | 3/2003 | Aronson et al. |

FOREIGN PATENT DOCUMENTS

| | | |
|---|---|---|
| EP | 0987008 A2 | 3/2000 |
| EP | 0987003 A2 | 3/2003 |
| WO | WO 97/17938 A | 5/1997 |
| WO | WO 01/08644 A1 | 2/2001 |
| WO | WO 01/70270 A2 | 9/2001 |
| WO | WO 01/76543 A1 | 10/2001 |

*Primary Examiner*—Shelly A. Dodson
(74) *Attorney, Agent, or Firm*—Cynthia L. Clay; John M. Howell; Tara M. Rosnell

(57) ABSTRACT

Rinsable skin conditioning compositions comprising high internal phase emulsions and being substantially free of surfactant provide superior deposition on skin of conditioning agents, skin benefit agents and/or other conventional cosmetic or skin care ingredients. Such rinsable skin conditioning compositions have much improve aesthetics as well.

27 Claims, No Drawings

RINSABLE SKIN CONDITIONING COMPOSITIONS

CROSS REFERENCE TO RELATED APPLICATIONS

This application is a continuation of U.S. application Ser. No. 10/142,217, filed May 9, 2002 now abandoned.

FIELD OF THE INVENTION

The present invention relates to rinsable, skin conditioning compositions. More particularly it relates to skin conditioning compositions comprising high internal phase emulsions substantially free of surfactant.

BACKGROUND OF THE INVENTION

Skin conditioning compositions that provide moisturizing benefits are known. Many of these compositions are aqueous systems comprising an emulsified conditioning oil or other similar material stabilized with surfactant. Typically, skin moisturizing compositions are in the form of lotions meant to be applied to the skin after bathing and throughout the day if reapplication is necessary.

Skin is made up of several layers of cells, which coat and protect the keratin and collagen fibrous proteins that form the skeleton of its structure. The outermost of these layers, referred to as the stratum corneum, is known to be composed of 25 nm protein bundles surrounded by 8 nm thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognized that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue, and the skin begins to scale and becomes itchy. Skin permeability is also decreased somewhat when there is inadequate water across the stratum corneum. On the other hand, exposure to high water concentration for long periods of time on the outside of the skin causes the stratum corneum to ultimately sorb three to five times its own weight of bound water. This swells and puckers the skin and results in approximately a two to three fold increase in the permeability of the skin to water and moisturizer molecules. In the shower or bath, as skin becomes hydrated, this is recognized as an ideal time to deliver moisturizer to the skin since absorption of the moisturizer will be high.

It is further desirable to deliver the above skin conditioning benefits via an in-the-shower or in-the-bath lotion. Unfortunately, in the shower/bath, moisturizers are often readily rinsed from the skin. This is particularly true when surfactant is present.

Thus, a need exists for compositions, which will effectively deposit moisturizers and/or other skin benefit agents in the shower and/or bath and thereby assist the stratum corneum in maintaining its barrier and water-retention functions at optimum performance in spite of deleterious interactions which the skin may encounter in washing, work, and recreation.

Desirable properties of such skin care compositions are to provide good skin feel, water retention, moisturization, absorption, and rub-in characteristics. One way of delivering high moisturization to the skin is to incorporate polyhydric alcohol-like humectant materials such as glycerine into a composition. Skin compositions with high levels of polyhydric alcohols and therefore high levels of moisturization when left-on the skin, however, are readily rinsed away in the shower and/or bath by the consumer. An alternative way of delivering desirable benefits to the skin is to incorporate oil-soluble skin care ingredients such as petrolatum into skin care compositions. Compositions, which incorporate the oil as an oil-in-water emulsion, must stabilize the emulsion which is generally done with surfactant (typically nonionic surfactant for lotions and anionic or amphoteric surfactant for lathering products). Again, such compositions when stabilized with surfactant, deposit poorly on the skin due to emulsification of the oil by the surfactant.

Another method previously used to deposit oil more effectively is to deliver the oil via a water-in-oil emulsion. Such compositions however, have big trade-offs in terms of poor (greasy) aesthetics, poor spreading on skin and creation of unsafe, slippery shower and/or tub floors.

It is a tremendous challenge to deposit effective amounts of skin conditioning ingredients on skin via a rinsable skin conditioning composition that also has excellent consumer acceptance. While not wishing to be bound by theory, it is believed that the oil soluble conditioning agents are easily emulsified by the surfactant present in most body wash and body lotion compositions. Therefore, the conditioning agents are rinsed away during the personal cleansing process. Although attempts have been made to formulate two-in-on body wash products that not only cleanse the skin, but additionally deliver skin moisturization, they don't generally deposit sufficient amount of skin conditioning ingredients to deliver the same level of skin moisturization as a leave-on lotion. This inadequate conditioning leaves consumers with an unmet need.

Accordingly, the need remains for a rinsable, skin-conditioning composition that can provide improved conditioning and other skin care benefits to human skin. Additionally, there remains a need for a rinsable, skin-conditioning composition which exhibits pleasing tactile properties and increased deposition of skin conditioning and/or skin care agents. The need also remains for in-shower and/or bath lotion compositions which show low levels of stickiness or tackiness whilst providing high levels of moisturization, as well as providing excellent skin feel, skin softness and skin smoothness benefits.

It has now been unexpectedly found that compositions comprising high internal phase oil-in-water emulsions show excellent oil deposition, excellent moisturization benefits, with low levels of stickiness or tack and superior product stability. These compositions can be formulated at surprisingly high viscosities while maintaining excellent spreadability on wet skin. The compositions also show good skin feel, skin softness and skin smoothness benefits. Other benefits in using high internal phase emulsions are that they are very easy to manufacture, they give the formulated great control over oil droplet size, they are low irritating and they allow for emulsification of previously incompatible materials in the same product. These and other benefits will be discussed in greater detail below.

The present invention provides rinsable, skin-conditioning compositions, which may further comprise skin benefit agents. These compositions provide improved aesthetics and skin feel during and/or after application, and are especially useful in providing improved deposition or effectiveness of skin conditioning agents to the desired area of the skin. The benefits of the compositions of the present invention are further improved The present invention further provides a method of conditioning the skin using the described compositions.

SUMMARY OF THE INVENTION

The present invention meets the aforementioned needs by providing a rinsable skin conditioning composition comprising a an oil-in-water emulsion wherein the composition has a Deposition Efficiency (DE) of at least about 2% wherein DE=[$W_{after}-W_0$]/[$W_{before}-W_0$]×100. The present invention further relates to a rinsable skin conditioning composition comprising (a) at least one high internal phase emulsion comprising (i) an oil; (ii) a stabilizer; (iii) water; and (b) the balance being conventional cosmetic and skin care ingredients.

The present invention further relates to a rinsable skin conditioning composition wherein the composition comprises (i) from about 20% to about 90% by weight of the oil; (ii) from about 0.1% to about 10% by weight of the stabilizer; (iii) from about 9.5% to about 79.5% by weight of water; and (iv) from about 0% to about 2% by weight of a perfume The present invention further relates to an article of commerce comprising a container comprising a rinse off skin conditioning composition, which provides skin conditioning and/or moisturizing benefits to the human skin when applied in the shower and/or bath and rinsed and comprises I. at least one high internal phase emulsion comprising an oil, a stabilizer, water and II. the balance being conventional cosmetic and skin care ingredients, wherein the composition is substantially free of surfactant and wherein said container has instructions for conditioning and moisturizing the skin comprising the instructions to wash skin and rinse as normal, smooth product onto skin while out of the flow of water, rinse briefly, and pat dry with towel.

The present invention further relates to a method of conditioning the skin comprising the steps of (A) preparing a rinsable skin condition composition comprising at least one high internal phase emulsion comprising I. (i) an oil; (ii) a stabilizer; (iii) water; and II. the balance being conventional cosmetic and skin care ingredients, wherein the composition is substantially free of surfactant; (B) applying the product of step (A) to wet human skin; and (C) rinsing the product off of the skin.

All documents cited are, in relevant part, incorporated herein by reference; the citation of any document is not to be construed as an admission that it is prior art with respect to the present invention.

DETAILED DESCRIPTION

The specific embodiments of the present invention will be described in detail below.

The term "ambient conditions" as used herein, unless otherwise specified, refers to surrounding conditions at one (1) atmosphere of pressure, 50% relative humidity, and 25° C.

The term "skin conditioning composition" as used herein, unless otherwise specified, refers to the compositions of the present invention, wherein the compositions are intended for topical application to the skin.

The term "rinsable" as used herein, unless otherwise specified, refers to compositions that can be both rinsed off the skin after application or left on depending upon the desire of the user.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The skin conditioning compositions and methods of the present invention can comprise, consist of, or consist essentially of, the essential elements and limitations of the invention described herein, as well as any additional or optional ingredients, components, or limitations described herein or otherwise useful in skin conditioning compositions intended for topical application to the hair or skin.

Product Form

The rinsable skin conditioning compositions of the present invention are liquid or semi-liquid, cream or mousse compositions intended for topical application to the skin. The product forms contemplated for purposes of defining the compositions and methods of the present invention are typically rinsable formulations, by which is meant the product is applied topically to the skin and then subsequently (i.e., within minutes) rinsed away with water, or otherwise wiped off using a substrate or other suitable removal means. However, it is contemplated that the subject compositions may be used as leave-on lotions as well without deviating from the spirit of the invention.

All elements of the present invention will be described in detail hereafter.

High Internal Phase Emulsion

The rinsable skin conditioning compositions of the present invention comprise at least one high internal phase (HIP) emulsion comprising an oil, a stabilizer, and water. The compositions are substantially free of surfactant including anionic, amphoteric, zwitterionic, cationic or nonionic surfactant. By "substantially free" is meant that the compositions comprise less than about 3%, preferably less than about 1%, more preferably less than about 0.5%, even more preferably less than about 0.25%, and most preferably less than about 0.1% surfactant. Optionally, the compositions may contain other skin benefit agents and conventional cosmetic or skin care ingredients.

The main difference between HIP emulsions and conventional emulsions is that HIP emulsions use high oil-packing to build viscosity.

Oils

The rinsable skin conditioning compositions of the present invention typically comprise from about 20% to about 90% of oil, more preferably 25 to 70% oil, even more preferably from 25 to 60% oil and most preferably from 30% to 40%. Oils suitable for use herein include any natural and synthetic materials with an overall solubility parameter less than about 12.5 $(cal/cm^3)^{0.5}$, preferably less than about 11.5 $(cal/cm^3)^{0.5}$. Solubility parameters for the oils described herein are determined by methods well known in the chemical arts for establishing the relative polar character of a material. A description of solubility parameters and means for determining them are described by C. D. Vaughn, "Solubility Effects in Product, Package, Penetration and Preservation" 103 Cosmetics and Toiletries 47–69, October 1988; and C. D. Vaughn, "Using Solubility Parameters in Cosmetics Formulation", 36 J. Soc. Cosmetic Chemists 319–333, September/October, 1988.

By "overall solubility parameter" is meant that it is possible to use oils with higher solubility parameters than 12.5 $(cal/cm^3)^{0.5}$ if they are blended with other oils to reduce the overall solubility parameter of the oil mixture to less than about 12.5 (cal/cm$^3$)$^{0.5}$. For example, a small portion of diethylene glycol (sol par=13.61) could be blended with lanolin oil (sol par=7.3) and a cosolublizing agent to create a mixture that has a solubility parameter of less than 12.5(cal/cm$^3$)$^{0.5}$.

These oils include but are not limited to hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, micro-crystalline waxes, polyalkenes, paraffins, cerasin, ozokerite, polyethylene, perhydrosqualene, poly alpha olefins, hydrogenated polyisobutenes and combinations thereof.

Non-limiting examples of silicone oils suitable for use herein include dimethicone copolyol, dimethylpolysiloxane, diethylpolysiloxane, mixed C1–C30 alkyl polysiloxanes, phenyl dimethicone, dimethiconol, and combinations thereof. Preferred are non-volatile silicones selected from dimethicone, dimethiconol, mixed C1–C30 alkyl polysiloxane, and combinations thereof. Nonlimiting examples of silicone oils useful herein are described in U.S. Pat. No. 5,011,681 (Ciotti et al.).

Non-limiting examples of diglycerides and triglycerides suitable for use herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof. In addition any of the above oils that have been partially or fully hydrogenated are also suitable.

Non-limiting examples of acetoglyceride esters suitable for use herein include acetylated monoglycerides.

Non-limiting examples of alkyl esters suitable for use herein include isopropyl esters of fatty acids and long chain esters of long chain fatty acids, e.g. SEFA (sucrose esters of fatty acids). Lauryl pyrolidone carboxylic acid, pentaerthritol esters, aromatic mono, di or triesters, cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use herein include oleyl myristate, oleyl stearate, oleyl oleate, and combinations thereof.

Non-limiting examples of lanolin and lanolin derivatives suitable for use herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, hydroxylated lanolin, hydrogenated lanolin and combinations thereof.

Still other suitable oils include milk triglycerides (e.g., hydroxylated milk glyceride) and polyol fatty acid polyesters.

Still other suitable oils include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

Stabilizers

The rinsable skin conditioning compositions of the present invention typically comprise from about 0.1% to about 10% of a stabilizer, preferably from about 0.5% to about 5%, and more preferably from about 0.5% to about 3%. Preferred stabilizers are any stabilizers that reduce the surface tension of water to not less 60 mN/m at 25° C. as measured by standard surface tension apparati and methods known to those of ordinary skill in the art, for example ASTM D1331-89 (2001) Method A, "Surface Tension". Preferred stabilizers exhibit a minimum surface tension in water of 60 mN/m or higher. Suitable stabilizers promote stability of the oil in water emulsion by inhibiting coalescence of the oil droplets, and/or inhibiting phase separation of the oil and water phases.

Some suitable stabilizers are Pemulen TR-1 (Acrylates/C10-30 Alkyl Acrylate Crosspolymer-Noveon), Pemulen TR-2 (Acrylates/C10-30 Alkyl Acrylate Crosspolymer-Noveon), ETD 2020 (Acrylates/C10-30 Alkyl Acrylate Crosspolymer-Noveon), Carbopol 1382 (Acrylates/C10-30 Alkyl Acrylate Crosspolymer-Noveon), Natrosol CS Plus 330, 430, Polysurf 67 (Cetyl Hydroxyethyl Cellulose-Hercules), Aculyn 22 (Acrylates/Steareth-20 Methacrylate Copolymer-Rohm&Haas) Aculyn 25 (Acrylates/Laureth-25 Methacrylate copolymer-Rohm&Haas), Aculyn 28 (Acrylates/Beheneth-25 Methacrylate copolymer-Rohm&Haas), Aculyn 46 (Peg-150/Stearyl Alcohol/SMDI copolymer-Rohm&Haas) Stabylen 30 (Acrylates/Vinyl Isodecanoate-3V), Structure 2001 (Acrylates/Steareth-20 Itaconate copolymer-National Starch), Structure 3001 (Acrylates/Ceteth-20 Itaconate copolymer-National Starch), Structure Plus (Acrylates/Aminoacrylates/C10-30 Alkyl Peg 20 Itaconate copolymer-National Starch, Quatrisoft LM-200 (Polyquaternium-24), the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

Cyclodextrins are solubilized, water-soluble, uncomplexed cyclodextrins. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin.

It is also preferable to use a mixture of cyclodextrins. Such mixtures can complex with a wider range of perfume molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, and mixtures thereof.

Cyclodextrins particularly preferred for use herein are alpha cyclodextron, beta cyclodextron, hydroxypropyl alpha cyclodextrin, hydroxypropyl beta cyclodextrin, and a mixture thereof.

Water

The rinsable skin conditioning compositions of the present invention typically comprise from about 9.5% to about 79.5% of water.

Perfume Oils

Preferred compositions of the present invention may optionally contain perfume. Suitable perfumes are those known to those skilled in the cosmetic and fragrance arts. When present the perfumes can be added to compositions according to the present invention via conventional methods. When added via conventional methods the perfume ingredients can be added at amounts from about 0% to about 2% relative to the entire composition.

It is especially desirable to add perfumes via a HIP emulsion. Without being bound by theory it is believed that perfumes incorporated via HIP emulsions deposit onto the skin at higher rates. Therefore, these perfumes may provide the present compositions with longer lasting scents and thus provide a more pleasing experience for the consumer. The perfume containing HIP emulsion is prepared as described above and stabilized with the previously listed stabilizers. When incorporated via a separate HIP emulsion the HIP emulsion is formulated with from about 20% to about 70% of perfume oil by weight of the HIP emulsion. It is often advantageous to include cyclodextrin in the perfume high internal phase emulsion as it can provide residual, long lasting fragrance on skin. The overall concentration of the perfume in the total composition is from 0% to about 2% regardless of the method for incorporation.

Gel Networks

The skin conditioning composition of the present invention may comprise a gel network. The gel network includes a cationic surfactant, a solid fatty compound and water. The gel network is typically characterized by a viscosity of from about 5,000 cps to about 40,000 cps, preferably from about 10,000 cps to about 30,000 cps, and more preferably from about 12,000 cps to about 28,000 cps, as measured at 250° C., by means of a Brookfield Viscometer at shear rate of 1.0 rpm. Without intending to be limited by theory, it is believed that the gel network significantly improves deposition of the conditioning agents and/or other skin benefit agents onto skin.

In a highly preferred embodiment, the gel network is a lamellar gel network, which provides improved skin feel, spreadability of the compositions, and other substantial benefits. Generally, the preferred cationic surfactants in the lamellar gel network contain one or two long chain (e.g., C12–30) alkyl groups, and a tertiary or quaternary amine group. Tertiary amine groups having one or two C16–22alkyl chains are preferred.

Nonlimiting examples of cationic surfactants useful in the present invention include materials having the following CTFA designations: quaternium-8, quaternium-14, quaternium-18, quaternium-18methosulfate, quaternium-24, and mixtures thereof. Among the cationic surfactants preferred are those containing in the molecule at least one alkyl chain having at least 16 carbons.

Nonlimiting examples of such preferred cationic surfactants include: dioleyolethyl hydroxyethymonium methoulfate, behenyltrimethyl ammonium chloride available, for example, with trade name INCROQUAT TMC-80 from Croda and ECONOL TM22 from Sanyo Kasei(Osaka, Japan); cetyl trimethyl ammonium chloride available, for example, with tradename CA-2350 from Nikko Chemical (Tokyo, Japan), hydrogenated tallowalkyl trimethyl ammonium chloride, dialkyl (14–18) dimethyl ammonium chloride, ditallow alkyl dimethyl ammonium chloride, dihydrogenated tallow alkyl dimethylammonium chloride, distearyl dimethyl ammonium chloride, dicetyl dimethylammonium chloride, di(behenyl/arachidyl) dimethyl ammonium chloride, dibehenyl dimethyl ammonium chloride, stearyl dimethyl benzyl ammoniumchloride, stearyl propyleneglycol phosphate dimethyl ammonium chloride, stearoyl amidopropyl dimethyl benzyl ammonium chloride, stearoyl amidopropyldimethyl (myristylacetate) ammonium chloride, and N-(stearoyl colarnino formylmethyl) pyridinium chloride.

Also preferred as cationic surfactants are hydrophilically substituted cationic surfactants in which at least one of the substituents contain one or more aromatic, ether, ester, amido, or amino moieties present as substituents or as linkages in the radical chain, wherein at least one of the RI"-R' 04 radicals contain one or more hydrophilic moieties selected from alkoxy (preferably C,_C3 alkoxy), polyoxyalkylene (preferably C1_C3 polyoxyalkylene), alkylamido, hydroxyalkyl, alkylester, and combinations thereof. Preferably, the hydrophilically substituted cationic surfactant contains from 2 to about 10 nonionic hydrophile moieties located within the above stated ranges. Nonlimiting examples of hydrophilically substituted cationic surfactants useful in the present invention include the materials having the following CTFA designations: quaternium-16, quaternium-26, quaternium-27, quaternium-30, quaternium-33,quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylarnido ethyl hydroxyethylmonium salt, dialkylamidoethyl dimonium salt, dialkyloyl ethyl hydroxyethylamonium salt, dialkyloyl ethyidimonium salt, and mixtures thereof; for example, commercially available under the following tradenames; VARISOFT 110, VARISOFT 222, VARIQUAT K1215 and VARIQUAT 638 from Witco Chemicals (Greenwich, Conn., USA), MACKPIRO KLP, MACKPIRO WLK MACKPRO MLP, MACKPRO NSP, MACKPIRO NLW, MACKPIRO WWP, MACKPIRO NLP, MACKPRO SLP from McIntyre, ETHOQUAD 18/25, ETHOQUAD 0/12PG, ETHOQUAD C/25,ETHOQUAD S/25, and ETHODUOQUAD from Akzo, DEHYQUAT SP from Henkel (Germany), and ATLAS G265 from ICI Americas (Wilmington, Del.,io USA).

Salts of primary, secondary, and tertiary fatty amines are also suitable cationic surfactants. The alkyl groups of such amines preferably have from about to about 22 carbon atoms, and can be substituted or unsubstituted.

Particularly useful are amido substituted tertiary fatty amines. Such amines, as useful herein, include stearamidopropyldimethylamine, stearamidopropyldiethylamine, stearamidoethyldiethylamine, stearamidoethyldimethylamine, palmitamidopropyidimethylamine, paimitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyidiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, andarachidylbehenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, L-aspartic acid, and mixtures thereof; more preferably L-glutamic acid, lactic acid, citric acid.

The fatty alcohol compound and cationic surfactant are included in the skin conditioning composition at a level by weight of the total composition from about 0.1% to about 20%, preferably from about 0.1% to about 15%, more preferably from about 0.1% to about 10%.

The fatty alcohols useful herein are those having from about 14 to about 22 carbon atoms, preferably from about 16 to about 22 carbon atoms. These fatty alcohols are saturated and can be straight or branched chain alcohols.

Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein.

Also included herein are salts of these fatty acids. Non-limiting examples of fatty acids include lauric acid, palmitic acid, stearic acid, behenic acid, sebacic acid, and mixtures thereof.

Solid fatty compounds of a single compound of high purity are preferred.

Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity may provide good rinsability from the skin when the consumer rinses off the composition.

Commercially available solid fatty compounds useful herein include: cetyl alcohol, stearyl alcohol, and behenyl alcohol having trade names KONOL series available from Shinnihon Rika (Osaka, Japan), and NAA series available from NOF (Tokyo, Japan); pure behenyl alcohol having trade name 1-DOCOSANOL available from Wako Chemical (Osaka, Japan), various fatty acids having trade names NEO-FAT available from Akzo (Chicago, Ill., USA), HYSTRENE available from Witco Corp. (Dublin, Ohio, USA), and DERMA available from Vevy (Genova, Italy).

While poly fatty alcohols may form the gel network, mono fatty alcohols are preferred. Either the cationic surfactant, and/or the solid fatty compound may be first mixed with, suspended, and/or dissolved in water when forming a gel network.

Deposition Efficiency:

Compositions of the present invention provide deposition of the skin conditioning or skin benefit agents onto skin with a Deposition Efficiency (DE) of at least about 2%, preferably from about 3% to about 40%, more preferably from about 4% to about 30%, and most preferably from about 4% to about 20%, by weight of the total composition, wherein $DE=[W_{after}-W_0]/[W_{before}-W_0]\times100$. Deposition Efficiency is determined using the method described below.

The test method described below is used to determine the level of deposition of skin conditioning and other optional skin benefit agents.

Clear 3 mil thick polyethylene sheets are cut to 21.5 cm×32.0 cm. Both sides of the sheets are sprayed with ethanol, wiped with a paper towel and allowed to hang dry for a few hours. The initial weight of each sheet is measured using a 4-digit analytical balance and recorded as $W_0$.

A piece of thick, grooved vinyl shelf covering (i.e. "Groovy Easy Liner" for shelves) is clipped to a 10×13 inch plastic clipboard. The grooves are about 5 mm wide, spaced about 5 mm apart, and are about 1.6 mm thick with 0.55 mm thick valleys. The grooves run across the short direction of the clipboard, and serve to provide underlying texture.

One polyethylene sheet is attached to the clipboard using a clip, placing the sheet over the underlying grooved vinyl covering. 1 gram of rinsable skin conditioning composition is applied to the sheet and spread by hand on the sheet for 30 seconds to all edges of the sheet. The sheet is again weighed. This weight, prior to rinsing is recorded as $W_{before}$.

The sheet is rinsed for 30 seconds in warm water (100–105° F.), letting the water stream hit the top edge of the sheet and cascade down the length of the sheet. Water flow rate is between 210 and 230 ml/10 seconds. The sheet is hung to dry from one corner using a clothespin and dried overnight (e.g. at 120° F. at 5% relative humidity for greater than 8 hours). The sheet is weighed again the next day. This weight after rinsing is recorded as $W_{after}$.

The deposition efficiency is calculated as: Deposition Efficiency=$[W_{after}-W_0]/[W_{before}-W_0]\times100$.

Rheology

Compositions according to the present invention preferably have a yield stress of from about 20 to about 200 Pa., more preferably from about 30 to about 100 Pa., even more preferably from about 50 to about 90 Pa. Preferred compositions also have viscosity in the range of from about 1,000 to about 20,000 cP, preferably from about 1,500 to about 10,000 cP, even more preferably from about 2,000 to about 7,000 cP. Yield stress and viscosity can be measured using methods familiar to those with ordinary skill in the art as described below.

Yield Stress:

A rheometer with a 4 cm diameter parallel plate geometry at a gap setting of 1 mm, for example a TA Instruments AR 2000 controlled stress rheometer manufactured by TA Instruments-Waters LLC, New Castle, Del., 19720, is used. A composition is loaded onto the rheometer base plate at 25° C., and the upper plate is positioned at a distance 1 mm from the base plate, containing the composition between the plates. Without disturbing the composition, excess is removed to the edge of the plate with a spatula. Using a controller and a computer (provided with rheometer), the rheometer is programmed to increase stress on the sample from a starting value of 0.1 Pa to a final value of 1,000 Pa in a series of 50 steps per decade of stress at a logarithmic rate of increase, over a total measurement time of 3 minutes. Data are collected in an electronic file for analysis. First, data are plotted as the log of stress/Pa vs. log of strain, and the yield stress is determined. The yield stress, or stress at which product flow begins, is the point at which the data exhibit a transition from non-flow into flow, evident as a kink in the curve of the log stress vs. log strain curve. Data in the non-flow region are linearized by regression or simply drawing a straight line through the non-flow data; and data in the flow region are linearized by regression or drawing a similar straight line, and the intersection of the linear regressions or the straight lines is determined to be the yield stress. For preferred products, a pronounced yield stress is demonstrated as a sharp bend in the data curves at the yield stress, as the composition rapidly shifts from non-flow to flow with increasing stress. For compositions that do not exhibit a yield stress by this method, the yield stress is taken to be a low value, i.e., less than 1 Pa or even 0 Pa for fluids such as Newtonian fluids.

Viscosity:

To determine the viscosity of the composition, the same data obtained above are plotted as viscosity (centipoises, or cP) vs. shear rate (inverse seconds, or 1/sec). The viscosity at a shear rate of 100 1/seconds is easily determined by observation of the data, and can be interpolated from the viscosity-shear rate data if needed. If a shear rate of 100 1/sec is not reached even at the highest stress in this test, the composition isre-tested with a higher stress range using the same measurement time per stress decade (1 minute per stress decade) until a sufficiently high shear rate is obtained.

Optional Ingredients

The skin conditioning compositions of the present invention may further comprise other optional ingredients that may modify the physical, chemical, cosmetic or aesthetic characteristics of the compositions or serve as additional "active" components when deposited on the skin. The compositions may also further comprise optional inert ingredients. Many such optional ingredients are known for use in personal care compositions, and may also be used in the skin conditioning compositions herein, provided that such optional materials are compatible with the essential materials described herein, or do not otherwise unduly impair product performance.

The rinsable skin conditioning compositions of the present invention may optionally comprise from about 0.1% to about 0.75% of a conventional preservative. Non-limiting examples of preservatives which may be used in the compositions of the present invention are benzyl alcohol, methyl paraben, propyl paraben, DMDM hydantoin, methylchloroisothiaoline, methylisothiazolinone, imidazolidinyl urea phenoxyethanol, sodium benzoate, and benzoic acid. EDTA and salts thereof are often used to further enhance preservation.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention.

Additional optional ingredients may include Clays (silicates), either synthetic or natural, and are used to provide high temperature phase stability. Examples of a synthetic Clay is Laponite a synthetic layered silicate from 0.05 to 2%, most preferably from 0.075 to 1.0%. Also useful are Magnesium Aluminum Silicate clays such as Gelwhite MAS and natural clays such as bentonites of the name Gelwhite L. Both Gelwhite MAS and Gelwhite L are useful in the range of 0.1 to 1% and most preferably from 0.2 to 0.5%.

Other optional ingredients include silicone elastomer powders and fluids to provide any of a variety of product benefits, including improved product stability, application cosmetics, emolliency, conditioning, and so forth. The concentration of the silicone elastomers in the composition preferably ranges from about 0.1% to about 20%, more preferably from about 0.5% to about 10%, by weight of the composition. In this context, the weight percentages are based upon the weight of the silicone elastomers material itself, excluding any silicone-containing fluid that typically accompanies such silicone elastomers materials in the formulation process. The silicone elastomers suitable for optional use herein include emulsifying and non-emulsifying silicone elastomers, non-limiting examples of which are described in U.S. Ser. No. 09/613,266 (assigned to The Procter & Gamble Company).

Skin Benefit Agents

The skin conditioning compositions of the present invention may optionally further comprise a skin benefit agent suitable for use on the skin, and which is otherwise compatible with the other selected ingredients in the composition. The skin benefit agent can be blended with the oils previously described and included as part of the main high internal phase emulsion. In this case the oil functions as a carrier for the skin benefit agent. The skin benefit agent may also be included as part of a separate high internal phase emulsion. The skin benefit agent may also be included as an add-on ingredient wherein it is not part of any of the high internal phase emulsion premixes.

Non-limiting examples of skin benefit agents suitable for use herein are described in The CTFA Cosmetic Ingredient Handbook, Second Edition (1992), which includes a wide variety of cosmetic and pharmaceutical ingredients commonly used in the skin care industry, and which are suitable for use in the compositions of the present invention. Non-limiting examples of such skin benefit agents include abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-microbial agents (e.g., iodopropyl butylcarbamate), antioxidants, colorants, cosmetic astringents, cosmetic biocides, drug astringents, external analgesics, opacifying agents, pH adjusters, skin bleaching and lightening agents (e.g., hydroquinone, kojic acid, ascorbic acid, magnesium ascorbyl phosphate, ascorbyl glucosamine), skin-conditioning and/or moisturizing agents, i.e. glycerine, skin soothing and/or healing agents (e.g., panthenol and derivatives (e.g., ethyl panthenol), aloe vera, pantothenic acid and its derivatives, allantoin, bisabolol, and dipotassium glycyrrhizinate), retinoids, (e.g. retinol palmitate), tocopheryl nicotinate, skin treating agents, vitamins and derivatives thereof. In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed. The skin benefit agents are furthered described hereinafter in details.

A) Desquamation Actives

The skin benefit agent for use herein can include desquamation actives, preferred concentrations of which range from about 0.1% to about 10%, more preferably from about 0.2% to about 5%, even more preferably from about 0.5% to about 4%, by weight of the composition for non-surfactant containing actives and from about 0.1% to about 3%, more preferably from about 0.2% to about 3%, even more preferably from about 0.5% to about 3% for surfactant containing actives. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett.

Another desquamation system that is suitable for use herein contains salicylic acid and zwitterionic surfactants and is described in U.S. Pat. No. 5,652,228 to Bissett.

B) Anti-Acne Actives

The skin benefit agent for use herein can also include anti-acne actives, preferred concentrations of which range from about 0.01% to about 50%, more preferably from about 1% to about 20%, by weight of the composition. Non-limiting examples of anti-acne actives suitable for use herein include resorcinol, sulfur, salicylic acid, benzoyl peroxide, erythromycin, zinc, and other similar materials.

Other non-limiting examples of suitable anti-acne actives for use herein are described in U.S. Pat. No. 5,607,980, issued to McAtee et al, which description is incorporated herein by reference.

C) Anti-Wrinkle Actives/Anti-Atrophy Actives

The skin benefit agent for use herein can also include anti-wrinkle actives or anti-atrophy actives, including sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like). Also suitable is niacinamide.

Hydroxy acids as skin benefit agents herein include salicylic acid and salicylic acid derivatives, preferred concentrations of which range from about 0.01% to about 50%, more preferably from about 0.1% to about 10%, even more preferably from about 0.5% to about 2%, by weight of the composition.

Other non-limiting examples of suitable anti-wrinkle actives for use herein are described in U.S. Pat. No. 6,217,888, issued to Oblong et al.

D) Anti-Oxidants/Radical Scavengers

The skin benefit agent for use herein can also include anti-oxidants or radical scavengers, preferred concentrations of which range from about 0.1% to about 10%, more preferably from about 1% to about 5%, by weight of the composition.

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

E) Chelators

The skin benefit agent for use herein can also include chelating agents. As used herein, the term "chelating agent" or "chelator" refers to those skin benefit agents capable of removing a metal ion from a system by forming a complex so that the metal ion cannot readily participate in or catalyze chemical reactions.

The chelating agents as skin benefit agents for use herein are preferably formulated at concentrations ranging from about 0.1% to about 10%, more preferably from about 1% to about 5%, by weight of the composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995.

Preferred chelating agents for use in the active phase of the compositions of the present invention include furildioxime, furilmonoxime, and derivatives thereof.

F) Flavonoids

The skin benefit agent for use herein includes flavonoid compounds suitable for use on the hair or skin, preferred concentrations of which range from about 0.01% to about 20%, more preferably from about 0.1% to about 10%, more preferably from about 0.5% to about 5%, by weight of the composition.

Non-limiting examples of flavonoids compounds suitable for use as skin benefit agents include flavanones such as unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Among these flavanoid compounds, preferred are unsubstituted flavanone, methoxy flavanones, unsubstituted chalcone, 2',4-dihydroxy chalcone, isoflavone, flavone, and mixtures thereof, more preferably soy isoflavones.

Other non-limiting examples of flavanoid compounds suitable for use as skin benefit agents herein are described in U.S. Pat. Nos. 5,686,082 and 5,686,367.

G) Anti-Inflammatory Agents

The skin benefit agent for use in the present composition can include anti-inflammatory agents, preferred concentrations of which range from about 0.1% to about 10%, more preferably from about 0.5% to about 5%, by weight of the composition.

Non-limiting examples of steroidal anti-inflammatory agents suitable for use herein include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

Nonsteroidal anti-inflammatory agents are also suitable for use herein as skin benefit agents in the active phase of the compositions. Non-limiting examples of non-steroidal anti-inflammatory agents suitable for use herein include oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e,g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof.

Other non-limiting examples of suitable anti-inflammatory or similar other skin benefit agents include candelilla wax, bisabolol (e.g., alpha bisabolol), aloe vera, plant sterols (e.g., phytosterol), Manjistha (extracted from plants in the genus Rubia, particularly *Rubia Cordifolia*), and Guggal (extracted from plants in the genus Commiphora, particularly *Commiphora Mukul*), kola extract, chamomile, red clover extract, sea whip extract, and combinations thereof.

Other non-limiting examples of suitable anti-inflammatory or similar other skin benefit agents include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific non-limiting examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

H) Anti-Cellulite Agents

The skin benefit agent for use in the compositions of the present invention anti-cellulite agents, non-limiting examples of which include xanthine compounds such as caffeine, theophylline, theobromine, aminophylline, and combinations thereof.

I) Topical Anesthetics

The skin benefit agent for use in the present invention include topical anesthetics, non-limiting examples of which include benzocaine, lidocaine, bupivacaine, chlorprocaine, dibucaine, etidocaine, mepivacaine, tetracaine, dyclonine, hexylcaine, procaine, ketamine, pramoxine, phenol, pharmaceutically acceptable salts thereof, and combinations thereof.

J) Tanning Actives

The skin benefit agent for use in the present invention include tanning actives, preferred concentrations of which range from about 0.1% to about 20% by weight of the composition. Non-limiting examples of such tanning agents include dihydroxyacetone, which is also known as DHA or 1,3-dihydroxy-2-propanone.

K) Skin Lightening Agents

The skin benefit agent for use in the present invention can include skin lightening agents, preferred concentrations of which range from about 0.1% to about 10%, more preferably from about 0.2% to about 5%, more preferably from about 0.5% to about 2%, by weight of the composition. Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract) as well as titanium dioxide and zinc oxide. Non-limiting examples of skin lightening agents suitable for use herein also include those described in WO 95/34280, WO 95/07432, and WO 95/23780.

L) Skin Soothing and Skin Healing Actives

The skin benefit agent for use in the present invention include skin soothing and skin healing actives, preferred concentrations of which range from about 0.1% to about 30%, more preferably from about 0.5% to about 20%, still more preferably from about 0.5% to about 10%, by weight of the composition. Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate.

M) Antimicrobial Actives

The skin benefit agent for use in compositions of the present invention may include antimicrobial actives, preferred concentrations of which range from about 0.001% to about 10%, more preferably from about 0.01% to about 5%, and still more preferably from about 0.05% to about 2%, by weight of the compositions.

Non-limiting examples of antimicrobial actives for use herein includes β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione, clotrimazole, and combinations thereof.

N) Sunscreen Actives

The skin benefit agent for use in the present invention may comprise a sunscreen active, either organic or inorganic sunscreen actives. Among the inorganic sunscreens useful hererin are metallic oxides such as titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof.

The concentration of the sunscreen active for use in the composition preferably ranges from about 0.1% to about 20%, more typically from about 0.5% to about 10%, by weight of the composition. Exact amounts of such sunscreen actives will vary depending upon the sunscreen or sunscreens chosen and the desired Sun Protection Factor (SPF).

A wide variety of conventional organic sunscreen actives are also suitable for use herein, non-limiting examples of which include p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoyl-methane; etocrylene; octocrylene; [3-(4'-methylbenzylidene bornan-2-one), terephthalylidene dicamphor sulfonic acid and 4-isopropyl-di-benzoylmethane. Among these sunscreens, preferred are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis (hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and combinations thereof.

Non-limiting examples of other sunscreen actives suitable for use herein include those described in U.S. Pat. No. 4,937,370 issued to Sabatelli on Jun. 26, 1990, and U.S. Pat. No. 4,999,186 issued to Sabatelli & Spirnak on Mar. 12, 1991. Among those sunscreen actives described, preferred are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof. Especially preferred sunscreen actives include 4,4'-t-butylmethoxydibenzoylmethane, 2-ethylhexyl-p-methoxycinnamate, phenyl benzimidazole sulfonic acid, and octocrylene.

O) Visual Skin Enhancers

The skin benefit agent for use in compositions of the present invention may include visual skin enhancement ingredients. These include ingredients that mask the appearance of any number of skin imperfections such as age spot, fine lines, wrinkles, blemishes etc., including but not limited to titanium dioxide, zinc oxide and iron oxides. Also suitable for use herein are organic particulates that diffuse light when deposited on the skin. Preferred concentrations of these ingredients range from about 0.001% to about 10%, more preferably from about 0.01% to about 5%, and still more preferably from about 0.05% to about 2%, by weight of the compositions.

Method of Use

The present invention is also directed to methods of using the skin conditioning compositions of the present invention comprising the steps of:

(A) preparing a rinsable skin condition composition comprising at least one high internal phase emulsion comprising
   I. (i) an oil;
      (ii) a stabilizer;
      (iii) water; and
   II. the balance being conventional cosmetic and skin care ingredients,
wherein the composition is substantially free of surfactant;
(B) applying the product of step (A) to wet human skin; and
(C) rinsing the product off of the skin.

While not wishing to be bound by theory, it is believed that efficacy of the product can be linked to the ability of the consumer to understand the usage instructions and to use the product accordingly. The instruction set included may contain pictures or illustrations of the product being applied as well as written instructions. Therefore, the present invention also relates to an article of commerce comprising a container comprising a rinse off skin conditioning composition, which provides skin conditioning and moisturizing benefits to the human skin when applied in the shower and/or bath and rinsed and comprises:

I. at least one high internal phase emulsion comprising
   i) an oil
   ii) a stabilizer;
   iii) water; and
II. the balance being conventional cosmetic and skin care ingredients,
wherein the composition is substantially free of surfactant and wherein said container has instructions for conditioning and moisturizing the skin comprising the instructions to wash skin and rinse as normal, smooth product onto skin while out of the flow of water, rinse briefly, and pat dry with towel.

Method of Manufacture

The skin conditioning compositions of the present invention may be prepared by any known or otherwise effective technique, suitable for making and formulating the desired product form. Specific non-limiting examples of such methods as they are applied to specific embodiments of the present invention are described in the following examples. For illustration purposes only, the following suitable method of manufacture employs two high internal phase emulsion premixes, to prepare a single product. Depending upon the properties of the specific oils and stabilizers selected it will be recognized by one of skill in the art that certain modifications may need to be made to the manufacturing method. It is contemplated however, that one or any number of premixes can be made and mixed together to form the final product.

An oil premix is prepared as follows:
1. Add ambient temperature water to a vessel
2. Add stabilizer to water.
3. Heat and mix water and stabilizer with a propeller blade until it reaches 85° C.
4. Continue to mix at 85° C. until stabilizer is completely hydrated (viscosity will increase as stabilizer hydrates and then decrease when stabilizer is hydrated- approximately 30 minutes)
5. In a separate vessel add oil and heat and mix at 85° C.
6. Add oil to water/stabilizer mixture slowly and increase propeller blade speed.
7. Continue to mix for 5 minutes at 85° C.
8. Add preservative to mixture and decrease temperature to 75° C.

Any number of oil premixes can be prepared as described above and used alone or in combination with other oil premixes in a final product. Skin benefit agents can also be included in the oil premixes.

Fatty Alcohol Gel Network Main Mix

9. Add ambient temperature water to a vessel
10. Add Stearamidopropyl Dimethylamine and glutamic acid and stabilizer to water.
11. Heat and mix mixture with a propeller blade until it reaches 85° C.
12. Continue to mix at 85° C. until stabilizer is completely hydrated (viscosity will increase as stabilizer hydrates and then decrease when stabilizer is hydrated- approximately 30 minutes)
13. Add fatty alcohol to hot mixture and continue to mix until fatty alcohol is completely melted.
14. Transfer to high shear mixer for 5 minutes.

Add Oil Premixs

15. Oil premixs are cooled to 75° C. and passed through a static mixer (or mill) to achieve desired particle size if necessary then added into the fatty alcohol gel network main mix tank with agitation.

Add Optional Ingredients i.e. Preservative and Perfume

16. Add solid preservatives first and liquid preservatives next.
17. Mix slowly to move entire batch.
18. Cool mixture to 42° C. and add remaining preservatives, fragrance and other conventional ingredients.

Continue mixing for 15 minutes

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved cosmetics during and after application, including reduced greasy or sticky skin feel, and provides improved deposition or effectiveness of the skin conditioning agent delivered from each prepared composition.

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| water | 58.198 | 48.688 | 43.688 | 48.8 | 51.278 | 51.078 | 58.198 | 58.036 | 53.688 | 45.188 | 40.188 | 44.188 | 37.144 | 48.856 |
| petrolatum | 30.000 | 40.000 | 40.000 | 40.000 | 40.000 | 40.000 | 0.000 | 20.000 | 40.000 | 40.000 | 40.000 | 40.000 | 30.000 | 40.000 |
| shea butter | 0.000 | 0.000 | 0.000 | 0.000 | 0.000 | 0.000 | 30.000 | 10.000 | 0.000 | 0.000 | 0.000 | 0.000 | 0.000 | 0.000 |
| Dimethicone/ Dimethiconol | 5.000 | 5.000 | 5.000 | 5.000 | 5.000 | 5.000 | 5.000 | 0.000 | 0.000 | 5.000 | 5.000 | 5.000 | 0.000 | 2.000 |
| sunflower oil | 0.000 | 0.000 | 0.000 | 0.000 | 0.000 | 0.000 | 0.000 | 5.000 | 0.000 | 0.000 | 0.000 | 0.000 | 0.000 | 0.000 |
| glycerine | 0.000 | 0.000 | 5.000 | 0.000 | 0.000 | 0.000 | 0.000 | 0.000 | 0.000 | 0.000 | 0.000 | 0.000 | 5.000 | 5.000 |
| stearyl alcohol | 2.310 | 2.310 | 2.310 | 2.310 | 0.430 | 0.430 | 2.310 | 2.310 | 2.310 | 2.310 | 2.310 | 2.310 | 0.640 | 0.640 |
| cetyl alcohol | 1.290 | 1.290 | 1.290 | 1.290 | 0.240 | 0.240 | 1.290 | 1.290 | 1.290 | 1.290 | 1.290 | 1.290 | 0.360 | 0.360 |
| cetylhydroxy cellulose | 1.250 | 0.760 | 0.760 | 0.760 | 1.310 | 1.310 | 1.250 | 1.400 | 0.760 | 0.760 | 0.760 | 0.760 | 0.000 | 1.000 |
| perfume | 1.200 | 1.200 | 1.200 | 1.000 | 1.000 | 1.200 | 1.200 | 1.200 | 1.200 | 1.200 | 1.200 | 1.200 | 0.000 | 1.200 |
| glydant | 0.370 | 0.370 | 0.370 | 0.370 | 0.370 | 0.370 | 0.370 | 0.370 | 0.370 | 0.370 | 0.370 | 0.370 | 0.370 | 0.370 |
| phenoxytol | 0.250 | 0.250 | 0.250 | 0.250 | 0.250 | 0.250 | 0.250 | 0.250 | 0.250 | 0.250 | 0.250 | 0.250 | 0.250 | 0.250 |
| disodium EDTA | 0.120 | 0.120 | 0.120 | 0.120 | 0.120 | 0.120 | 0.120 | 0.120 | 0.120 | 0.120 | 0.120 | 0.120 | 0.120 | 0.120 |
| SAPDMA[1] | 0.009 | 0.009 | 0.009 | 0.006 | 0.002 | 0.002 | 0.009 | 0.018 | 0.009 | 0.009 | 0.009 | 0.009 | 0.003 | 0.003 |
| glutamic acid | 0.003 | 0.003 | 0.003 | 0.002 | 0.001 | 0.001 | 0.003 | 0.006 | 0.003 | 0.003 | 0.003 | 0.003 | 0.001 | 0.001 |
| propane/isobutane pentane propellant | 0.000 | 0.000 | 0.000 | 0.000 | 0.000 | 0.000 | 0.000 | 0.000 | 0.000 | 3.500 | 0.000 | 0.000 | 0.000 | 0.000 |
| $ZnO_2$ | 0.000 | 0.000 | 0.000 | 0.000 | 0.000 | 0.000 | 0.000 | 0.000 | 0.000 | 0.000 | 5.000 | 0.000 | 0.000 | 0.000 |
| tocopherol nicotinate | 0.000 | 0.000 | 0.000 | 0.000 | 0.000 | 0.000 | 0.000 | 0.000 | 0.000 | 0.000 | 0.000 | 1.000 | 0.000 | 0.000 |
| Pemulen TR-2 | 0.000 | 0.000 | 0.000 | 0.000 | 0.000 | 0.000 | 0.000 | 0.000 | 0.000 | 0.000 | 0.000 | 0.000 | 0.200 | 0.000 |
| Gel White L | 0.000 | 0.000 | 0.000 | 0.500 | 0.000 | 0.000 | 0.000 | 0.000 | 0.000 | 0.000 | 0.000 | 0.000 | 0.200 | 0.200 |

[1]Stearamidopropyl Dimethylamine

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rinsable skin conditioning composition comprising an oil-in-water emulsion wherein the composition has a Deposition Efficiency (DE) of at least about 2% wherein $DE=[W_{after}-W_0]/[W_{before}-W_0]\times100$.

2. A rinsable skin conditioning composition according to claim 1 wherein the composition has a viscosity from about 1,000 to about 20,000 cP.

3. A rinsable skin conditioning composition according to claim 1 wherein the composition has a yield stress from about 20 Pa. to about 200 Pa.

4. A rinsable skin conditioning composition comprising:
   (a) at least one high internal phase emulsion comprising
      (i) an oil;
      (ii) a stabilizer;
      (iii) water; and
   (b) the balance being conventional cosmetic and skin care ingredients.

5. A rinsable skin conditioning composition according to claim 4 wherein the composition is substantially free of surfactant.

6. A rinsable skin conditioning composition according to claim 4 further comprising a perfume wherein the perfume is present in a high internal phase emulsion.

7. A rinsable skin conditioning composition according to claim 4 further comprising a skin benefit agent wherein the skin benefit agent is added to the oil.

8. A rinsable skin conditioning composition according to claim 4 wherein the stabilizer selected from the group consisting of acrylate/$C_{10}$–$C_{30}$ alkyl acrylate crosspolymer, cetyl hydroxyethyl cellulose, acrylate/steareth-20 methacrylate copolymer, acrylate/laureth-25 methacrylate copolymer, acrylate/beheneth-25 methacrylate copolymer, PEG-150/stearyl alcohol/SMDI copolymer, acrylate/vinyl isodecanoate, acrylate/steareth-20 itaconate copolymer, acrylate/ceteth-20 itaconate copolymer, acrylate/aminoacrylate/$C_{10}$–$C_{30}$ alkyl PEG 20 itaconate copolymer, polyquaternium-24, the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

9. A rinsable skin conditioning composition according to claim 4 wherein the composition comprises:
   (i) from about 20% to about 90% by weight of the oil;
   (ii) from about 0.1% to about 10% by weight of the stabilizer;
   (iii) from about 9.5% to about 79.5% by weight of water; and
   (iv) from about 0% to about 2% by weight of a perfume.

10. A rinsable skin conditioning composition according to claim 9 wherein the composition is substantially free of surfactant.

11. A rinsable skin conditioning composition according to claim 4 wherein the oil is selected from the group consisting of hydrocarbon oils, waxes, silicones, derivatives of fatty acids, cholesterol, cholesterol derivatives, diglycerides, triglycerides, vegetable oils, vegetable oil derivatives, acetoglyceride esters, alkyl esters, alkenyl esters, lanolin, lanolin derivatives, wax esters, beeswax derivatives, sterols, phospholipids, and mixtures thereof.

12. A rinsable skin conditioning composition according to claim 4 wherein the composition has a Deposition Efficiency (DE) of at least about 2% wherein $DE=[W_{after}-W_0]/[W_{before}-W_0]\times100$.

13. An article of commerce comprising a container comprising a rinse off skin conditioning composition, which provides skin conditioning and moisturizing benefits to the human skin when applied in the shower or bath and rinsed and comprises:

I. at least one high internal phase emulsion comprising
  iv) an oil
  v) a stabilizer;
  vi) water; and
II. the balance being conventional cosmetic and skin care ingredients, wherein said container has instructions for conditioning and moisturizing the skin comprising the instructions to wash skin and rinse as normal, smooth product onto skin while out of the flow of water, rinse briefly, and pat dry with towel.

14. An article of commerce according to claim 13 wherein the skin conditioning composition is substantially free of surfactant.

15. An article of commerce according to claim 13 wherein said instructions comprise illustrations.

16. An article of commerce according to claim 13 wherein the stabilizer is selected from the group consisting of acrylate/$C_{10}$–$C_{30}$ alkyl acrylate crosspolymer, cetyl hydroxyethyl cellulose, acrylate/steareth-20 methacrylate copolymer, acrylate/laureth-25 methacrylate copolymer, acrylate/beheneth-25 methacrylate copolymer, PEG-150/stearyl alcohol/SMDI copolymer, acrylate/vinyl isodecanoate, acrylate/steareth-20 itaconate copolymer, acrylate/ceteth-20 itaconate copolymer, acrylate/aminoacrylate/$C_{10}$–$C_{30}$ alkyl PEG 20 itaconate copolymer, polyquaternium-24, the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

17. An article of commerce according to claim 13 wherein the composition further comprises a perfume and the perfume is present in a high internal phase emulsion.

18. An article of commerce according to claim 13 wherein the composition further comprises a skin benefit agent and the skin benefit agent is added to the oil.

19. An article of commerce according to claim 13 wherein the composition has a Deposition Efficiency (DE) of at least about 2% wherein DE=[$W_{after}$–$W_0$]/[$W_{before}$–$W_0$]×100.

20. An article of commerce according to claim 13 wherein the oil is selected from the group consisting of hydrocarbon oils, waxes, silicones, derivatives of fatty acids, cholesterol, cholesterol derivatives, diglycerides, triglycerides, vegetable oils, vegetable oil derivatives, acetoglyceride esters, alkyl esters, alkenyl esters, lanolin, lanolin derivatives, wax esters, beeswax derivatives, sterols, phospholipids, and mixtures thereof.

21. An article of commerce according to claim 13 wherein the composition comprises:
  (i) from about 20% to about 90% by weight of the oil;
  (ii) from about 0.1% to about 10% by weight of the stabilizer;
  (iii) from about 9.5% to about 79.5% by weight of water; and (iv) from about 0% to about 2% by weight of a perfume.

22. A method of conditioning the skin comprising the steps of:
  (A) preparing a rinsable skin condition composition comprising at least one high internal phase emulsion comprising
    I. (i) an oil;
      (ii) a stabilizer;
      (iii) water; and
    II. the balance being conventional cosmetic and skin care ingredients,
  (B) applying the product of step (A) to wet human skin; and
  (C) rinsing the product off of the skin.

23. A method of conditioning the skin according to claim 22 wherein the composition is substantially free of surfactant.

24. A method of conditioning the skin according to claim 22 wherein the stabilizer is selected from the group consisting of acrylate/$C_{10}$–$C_{30}$ alkyl acrylate crosspolymer, cetyl hydroxyethyl cellulose, acrylate/steareth-20 methacrylate copolymer, acrylate/laureth-25 methacrylate copolymer, acrylate/beheneth-25 methacrylate copolymer, PEG-150/stearyl alcohol/SMDI copolymer, acrylate/vinyl isodecanoate, acrylate/steareth-20 itaconate copolymer, acrylate/ceteth-20 itaconate copolymer, acrylate/aminoacrylate/$C_{10}$–$C_{30}$ alkyl PEG 20 itaconate copolymer, polyquaternium-24, the metal oxides of titanium, zinc, iron, zirconium, silicon, manganese, aluminium and cerium, polycarbonates, polyethers, polyethylenes, polypropylenes, polyvinyl chloride, polystyrene, polyamides, polyacrylates, cyclodextrins and mixtures thereof.

25. A method of conditioning the skin according to claim 22 wherein the composition comprises:
  (i) from about 20% to about 90% by weight of the oil;
  (ii) from about 0.1% to about 10% by weight of the stabilizer;
  (iii) from about 9.5% to about 79.5% by weight of water; and
  (iv) from about 0% to about 2% by weight of a perfume.

26. A rinsable skin conditioning composition according to claim 4 wherein the high internal phase emulsion is incorporated into a fatty gel network.

27. A method of using a rinsable skin conditioning composition on the skin, said method comprising the steps of:
  (A) obtaining a personal cleansing composition comprising at least one high internal phase emulsion comprising
    I. (i) an oil;
      (ii) a stabilizer;
      (iii) water; and
    II. the balance being conventional cosmetic and skin care ingredients,
  wherein the composition is substantially free of surfactant; and
  (B) providing instructions with the rinsable skin conditioning composition to perform the following usage steps;
    a) wash and rinse skin as normal,
    b) smooth product onto skin while out of the water,
    c) rinse briefly, and
    d) pat dry.

* * * * *